United States Patent [19]

Krämer et al.

[11] Patent Number: 4,921,967

[45] Date of Patent: May 1, 1990

[54] NOVEL ALKYLCYCLOALKYL TRIAZOLYLMETHYL KETONES AS FUNGICIDE INTERMEDIATES

[75] Inventors: Wolfgang Krämer, Wuppertal; Manfred Jautelat, Burscheid; Eckart Kranz, Wuppertal, all of Fed. Rep. of Germany

[73] Assignee: Bayer Aktiengesellschaft, Leverkusen, Fed. Rep. of Germany

[21] Appl. No.: 54,551

[22] Filed: May 27, 1987

Related U.S. Application Data

[63] Continuation of Ser. No. 438,086, Nov. 1, 1982, abandoned.

[30] Foreign Application Priority Data

Nov. 19, 1981 [DE] Fed. Rep. of Germany ....... 3145857

[51] Int. Cl.$^5$ .............................. C07D 249/08
[52] U.S. Cl. .................................. 548/267.8
[58] Field of Search .......................... 548/262

[56] References Cited

U.S. PATENT DOCUMENTS

| | | |
|---|---|---|
| 4,079,143 | 3/1978 | Balasubramanyan et al. ...... 548/262 |
| 4,315,764 | 2/1982 | Reiser et al. ................... 548/262 |
| 4,554,007 | 11/1985 | Funaki et al. .................. 548/262 |
| 4,582,843 | 4/1986 | Timmler et al. ................. 548/262 |

FOREIGN PATENT DOCUMENTS

| | | | |
|---|---|---|---|
| 040345 | 2/1981 | European Pat. Off. ........... | 548/262 |
| 1464224 | 2/1977 | United Kingdom ............... | 548/262 |

Primary Examiner—Glennon H. Hollrah
Assistant Examiner—Patricia L. Morris
Attorney, Agent, or Firm—Sprung Horn Kramer & Woods

[57] ABSTRACT

New alkylcycloalkyl triazolylmethyl ketones of the general formula

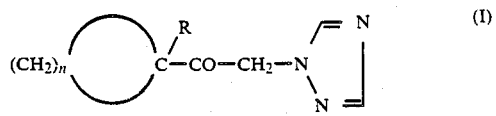

in which
R represents an alkyl group and
n is 3, 4, 5, 6 and 7, are produced as described and find use as intermediate products for the preparation of cycloalkyl (α-triazolyl-β-hydroxy)-ketones, which possess fungicidal and plant growth-regulating properties.

1 Claim, No Drawings

NOVEL ALKYLCYCLOALKYL TRIAZOLYLMETHYL KETONES AS FUNGICIDE INTERMEDIATES

This is a continuation of Application Ser. No. 438,086, filed Nov. 1, 1982, now abandoned.

The present invention relates to certain new alkylcycloalkyl triazolylmethyl ketones, to an unobvious process for their production, and to their use as intermediate products for the synthesis of cycloalkyl ($\alpha$-triazolyl-$\beta$-hydroxy)-ketones, which possess fungicidal and plant growth-regulating properties.

It has already been disclosed that certain alkyl or phenyl ($\alpha$-triazolyl-$\beta$-hydroxy)-ketones possess good fungicidal properties (see U.S. Pat. No. 4,291,047). Thus, for example, 1,1,1-trichloro-2-hydroxy-3-(1,2,4-triazol-1-yl)-4-(4-chlorophenyl)-butan-4-one and 2-chloro-3-hydroxy-2,7,7-trimethyl-4-(1,2,4-triazol-1-yl)-heptan-5-one can be employed for combating fungi. However, the action of these substances is not always entirely satisfactory, particularly when low amounts and concentrations are used.

The present invention now provides, as new compounds, the alkylcycloalkyl triazolylmethyl ketones of the general formula

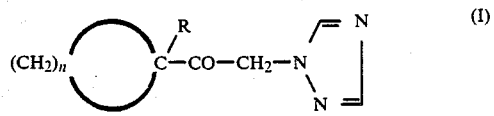

in which
R represents an alkyl group and
n is 3, 4, 5, 6 or 7.

According to the present invention we further provide a process for the production of an alkylcycloalkyl triazolylmethyl ketone of the present invention, characterized in that an alkylcycloalkyl halogenomethyl ketone of the general formula

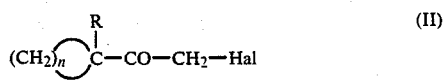

in which
R and n have the meanings given above and
Hal represents a chlorine or bromine atom,
is reacted with triazole of the formula

in the presence of a diluent and in the presence of an acid-binding agent.

The new alkylcycloalkyl triazolylmethyl ketones are interesting intermediate products for the preparation of active compounds for plant protection. Thus, the substances of the formula (I) are suitable starting materials for the synthesis of cycloalkyl ($\alpha$-triazolyl-$\beta$-hydroxy)-ketones, which possess very good fungicidal and plant growth-regulating activity.

Surprisingly, the cycloalkyl ($\alpha$-triazolyl-$\beta$-hydroxy)-ketones, which can be prepared from the alkylcycloalkyl triazolylmethyl ketones according to the invention, of the formula (I), by reaction with aldehydes, have a superior fungicidal activity compared with the compounds 1,1,1-trichloro-2-hydroxy-3-(1,2,4-triazol-1-yl)-4-(4-chlorophenyl)-butan-4-one and 2-chloro-3-hydroxy-2,7,7-trimethyl-4-(1,2,4-triazol-1-yl)-heptan-5-one which are known from the prior art. In addition, the cycloalkyl ($\alpha$-triazolyl-$\beta$-hydroxy)-ketones which can be prepared from the compounds according to the invention, of the formula (I), are also unexpectedly distinguished by very good plant growth-regulating properties.

Preferred compounds of formula (I) according to the invention are those
in which
R represents a straight-chain or branched alkyl group having 1 to 6 carbon atoms and
n has the meaning given above.

Those compounds of the formula (I) in which R represents a methyl or ethyl group, are particularly preferred.

In addition to the compounds mentioned in the examples hereinbelow, the following compounds of the formula (I) may be mentioned individually:

TABLE 1

| R | n |
|---|---|
| CH$_3$ | 3 |
| CH$_3$ | 4 |
| CH$_3$ | 6 |
| CH$_3$ | 7 |
| C$_2$H$_5$ | 3 |
| C$_2$H$_5$ | 5 |
| C$_2$H$_5$ | 6 |
| C$_2$H$_5$ | 7 |

If, for example, 1-chloroacetyl-1-ethylcyclopentane and 1,2,4-triazole are used as starting materials, the course of the reaction in the process according to the invention can be represented by the following equation:

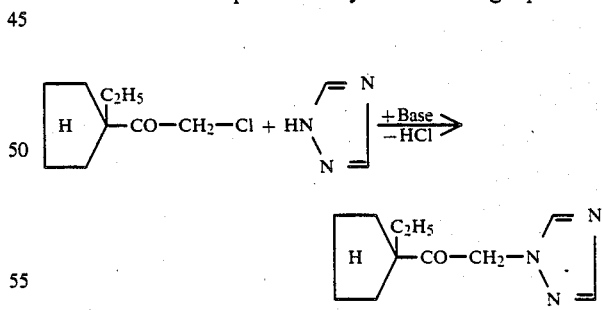

Preferred alkylcycloalkyl halogenomethyl ketones of formula (II) required as starting materials for carrying out the process according to the invention are those in which R has the meaning given for this radical in connection with the description of the preferred and particularly preferred compounds according to the invention, and Hal and n have the meanings given above.

The alkylcycloalkyl halogenomethyl ketones of the formula (II) were hitherto unknown. However, they can be prepared in a simple manner according to processes which are known in principle. Thus, an alkylcycloalkyl halogenomethyl ketone of the formula (II) is obtained by reacting a 1,1-dichloroalkene of the general formula

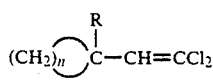 (IV)

in which R and n have the meanings given above, with a phenolate of the general formula

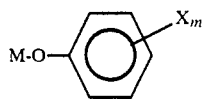 (V)

in which

M represents one equivalent of an alkali metal ion or alkaline earth metal ion, especially a sodium ion or potassium ion, X represents a halogen atom, or an alkyl or alkoxy group, each having 1 to 3 carbon atoms, or a phenyl group, and m is 0, 1 or 2, in the presence of an inert organic solvent, (such as dimethylformamide), at a temperature between 100° and 220° C., if appropriate under elevated pressure, and hydrolyzing the resulting phenyl ether of the general formula

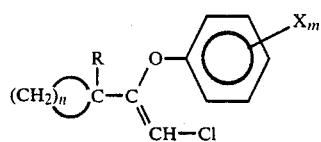 (VI)

in which R, X, m and n have the meanings given above, in a customary manner with a mineral acid (such as sulphuric acid or hydrochloric acid) and/or an organic acid (such as formic acid), at 40° to 100° C.

The preparation of 1,1-dichloroalkenes of the formula (IV) is known. It is effected by the addition reaction of alkyl halides with vinylidene chloride in the presence of acidic catalysts (in this context, see J. Am. Chem. Soc. 74, 2, 885 (1952)), hydrogen halide being split off at the same time.

The phenolates of the formula (V) are generally known compounds of organic chemistry.

The alkylcycloalkyl halogenomethyl ketones of the formula (II) can also be obtained when alkylcycloalkyl methyl ketone of the general formula

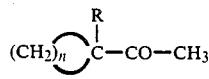 (VII)

in which R and n have the meanings given above, is reacted in the customary manner with chlorine or bromine in the presence of an inert organic solvent (such as ethers, or chlorinated or unchlorinated hydrocarbons), at room temperature, or is reacted with a customary chlorinating agent (such as sulphuryl chloride), at 20° to 60° C.

The alkylcycloalkyl methyl ketones of the formula (VII) are obtained when a corresponding nitrile of the general formula

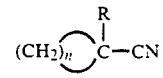 (VIII)

in which R and n have the meanings given above, is reacted in the customary manner with an organometallic compound, (such as, especially, methyl magnesium bromide) in the presence of a diluent (such as an anhydrous ether), at a temperature between 0° and 80° C.

Nitriles of the formula (VIII) are known (see Journal of Organometallic Chemistry 57, C 33–35 (1973)), and they can be obtained according to the processes given in this publication.

Suitable diluents for the process according to the invention are inert organic solvents. These include, as preferences, ketones (such as acetone, methyl ethyl ketone and methyl butyl ketone), alcohols (such as ethanol, isopropanol and butanol), aromatic hydrocarbons (such as benzene and toluene), formamides and sulphoxides (such as dimethylformamide and dimethylsulphoxide).

The process according to the invention is carried out in the presence of an acid-binding agent. It is possible to add any of the customarily usable inorganic or organic acid-binding agents, such as alkali metal carbonates (for example sodium carbonate, potassium carbonate and sodium bicarbonate), alkali metal hydroxides and alkaline earth metal hydroxides (for example potassium hydroxide and calcium hydroxide), or lower tertiary alkylamines, cycloalkylamines or aralkylamines (for example triethylamine, N,N-dimethylmethylcyclohexylamine, dicyclohexylamine and N,N-dimethylbenzylamine, furthermore pyridine and diazabicyclooctane).

Preferably, an appropriate excess of triazole is used.

In the process according to the invention, the reaction temperature can be varied within a relatively wide range. In general, the reaction is carried out at a temperature between 0° and 120 C., preferably between 20° and 90° C. Advantageously, the reaction is carried out at the boiling point of the particular solvent.

In carrying out the process according to the invention, 1 to 4 mols of azole and 1 to 4 moles of the acid-binding agent are preferably employed per mol of the compound of the formula (II). To isolate the compound of the formula (I), the solvent is distilled off and the residue is worked up in the customary manner.

The alkylcycloalkyl triazolylmethyl ketones according to the invention, of the formula (I), are suitable intermediate products for the synthesis of cycloalkyl (α-triazolyl-β-hydroxy)-ketones, which possess fungicidal and plant growth-regulating activity.

Such cycloalkyl (α-triazolyl-β-hydroxy)-ketones of the general formula

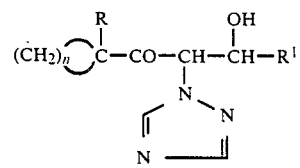 (IX)

in which

R and n have the meanings given above and

R¹ represents a halogenoalkyl, halogenoalkenyl or alkoxycarbonyl group, can be prepared by reacting an alkylcycloalkyl triazolylmethyl ketone of the general formula

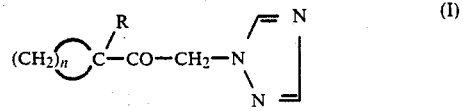 (I)

in which R and n have the meanings given above, with an aldehyde of the general formula

 (X)

in which R¹ has the meaning given above, in the presence of a diluent and in the presence of a catalyst.

Preferred aldehydes of formula (X) to be used as reactants in this reaction are those in which R¹ represents a straight-chain or branched halogenoalkyl group having 1 to 4 carbon atoms and 1 to 5 identical or different halogen atoms (such as, especially, fluorine, chlorine or bromine), a straight-chain or branched halogenoalkenyl group having 2 to 4 carbon atoms and 1 to 5 identical or different halogen atoms (such as, especially, fluorine, chlorine or bromine), or an alkoxycarbonyl group having 1 to 4 carbon atoms in the alkoxy part.

The aldehydes of the formula (X) are generally known compounds of organic chemistry.

Any of the inert organic solvents are suitable diluents for the reaction of the alkylcycloalkyl triazolylmethyl ketones according to the invention, of the formula (I), with aldehydes of the formula (X). Preferred diluent are alcohols (such as methanol and ethanol), and their mixtures with water; ethers (such as tetrahydrofuran and dioxane); nitriles (such as acetonitrile and propionitrile); halogenated aliphatic and aromatic hydrocarbons (such as methylene chloride, carbon tetrachloride, chloroform, chlorobenzene and dichlorobenzene); and glacial acetic acid.

The process, given above, for the preparation of cycloalkyl (α-triazolyl-β-hydroxy)-ketones is carried out in the presence of a catalyst. Any of the acidic and, especially, basic catalysts which can customarily be used for reactions of this type can be employed in this process. These include, as preferences, Lewis acids (such as iron (III) chloride, iron (III) bromide, boron trifluoride, boron trichloride, tin tetrachloride or titanium tetrachloride), alkali metal hydroxides and alkaline earth metal hydroxides (such as potassium hydroxide, sodium hydroxide, calcium hydroxide or barium hydroxide), alkali metal salts (such as potassium carbonate, sodium carbonate, potassium cyanide, secondary sodium phosphate, sodium acetate and sodium sulphite) and alcoholates (such as sodium ethylate or potassium ethylate).

In the process, given above, for the preparation of cycloalkyl (α-triazolyl-β-hydroxy)-ketones of formula (IX), the reaction temperatures can be varied within a relatively wide range. In general, the reaction is carried out at a temperature between 0° C. and 100° C., preferably at room temperature or at the boiling point of the particular solvent.

In carrying out the process, given above, for the preparation of cycloalkyl (α-triazolyl-β-hydroxy)ketones of formula (IX), the reactants of the formulae (I) and (X) are employed in general in equimolar amounts. In addition, a catalytic amount, or even equimolar amounts, of the catalyst are added. It is also possible to employ one of the reactants of the formulae (I) and (X) in an excess. The compounds of the formula (IX) are isolated in the customary manner.

The cycloalkyl (α-triazolyl-β-hydroxy)-ketones of the formula (IX) which can be prepared from the substances according to the invention possess very good fungicidal and plant growth-regulating properties. In particular, they can be employed for combating those fungi which cause powdery mildew diseases.

EXAMPLE 1

(a)

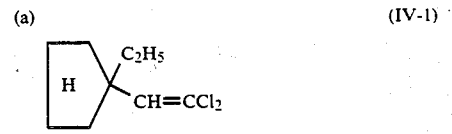 (IV-1)

10 g of anhydrous aluminum chloride were added to 291 g (3 mol) of 1,1-dichloroethene at −20° C., and thereafter 133 g (1 mol) of 1-ethyl-cyclopentyl chloride (Chem. Abstr. 42, 6,328 (1948)) were added dropwise at 0° to 10° C. The reaction solution was allowed to warm up to 20° C., a further 5 g of aluminum chloride were added, and stirring was continued for a further 2 hours at 20° C. The mixture was poured onto ice, and was worked up with methylene chloride and dilute hydrochloric acid. 158 g (82% of theory) of 1-(2,2-dichlorovinyl)-1-ethylcyclopentane of boiling point 45° to 50° C./0.1 mm Hg were obtained by fractional distillation of the organic phase after it had been dried over sodium sulphate.

(b)

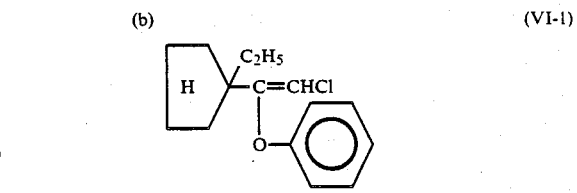 (VI-1)

140 g (4.2 mol) of sodium phenolate in 500 ml of N-methylpyrrolidone were heated to 200° C. 116 g (0.6 mol) of 1-(2,2-dichlorovinyl)-1-ethyl-cyclopentane were added dropwise so slowly that the reaction temperature did not fall below 195° C. The mixture was then stirred for a further hour at 210° C. After the mixture had cooled, it was diluted with methylene chloride and extracted several times by shaking with 2N sodium hydroxide solution. The organic phase, which had been dried over sodium sulphate, was concentrated in vacuo, and the residue was fractionated. 132 g (88% of theory) of 1-chloro-2-(1-ethylcyclopentyl)-2-phenoxy-ethylene of boiling point 115° to 125° C./0.1 mm Hg were obtained.

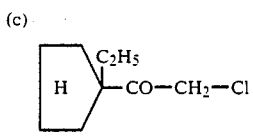
(II-1)

125.3 g (0.5 mol) of 1-chloro-2-(1-ethylcyclopentyl)-2-phenoxyethylene in 500 ml of formic acid and 50 ml of concentrated hydrochloric acid were heated at 80° C. for 2 hours. The mixture was then diluted with methylene chloride and ice, and was extracted three times by shaking with 2N sodium hydroxide solution. After the methylene chloride phase had been dried over sodium sulphate, the solvent was evaporated off in vacuo, in a rotary evaporator. The residue was distilled in vacuo. 72 g (82.6% of theory) of 1-chloroacetyl-1-ethylcyclopentane of refractive index $n_D^{20} = 1.484$ were obtained.

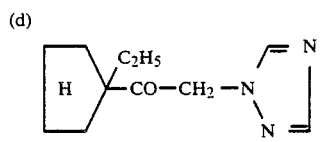
(1)

52.5 g (0.3 mol) of 1-chloro-acetyl-ethylcyclopentane, 42 g of potassium carbonate and 72 g of 1,2,4-triazole were dissolved in 400 ml of ethanol, and the solution was stirred for 48 hours at 20° C. The solvent was distilled off in vacuo, the residue was taken up in 500 ml of water, and the solution was stirred with 300 ml of methylene chloride. The organic phase was separated off, washed several times with 100 ml portions of water, dried over sodium sulphate and concentrated in vacuo. The residue slowly crystallized completely. 50 g (81% of theory) of 1-ethylcyclopentyl (1,2,4-triazol-1-yl)-methyl ketone of refractive index $n_D^{20} = 1.5027$ were obtained.

EXAMPLE 2

Preparation of a Secondary Product

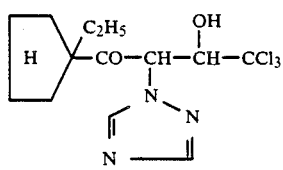
(IX-1)

9.3 g (0.064 mol) of chloral were added dropwise to 10.4 g (0.05 mol) of 1-ethylcyclopentyl (1,2,4-triazol-1-yl)methyl ketone (prepared as described in Example 1) and 13.8 g (0.1 mol) of ground potassium carbonate in 100 ml of tetrahydrofuran. The reaction mixture was stirred overnight at room temperature and was then stirred with water. The solid formed was filtered off under suction and recrystallized from ethyl acetate. 7 g (39.5% of theory) of 1,1,1-trichloro-2-hydroxy-3-(1,2,4-triazol-1-yl)-4-(1-ethylcyclopentan-1-yl)-butan-4-one of melting point 194° to 196° C. were obtained.

The starting materials of the formula

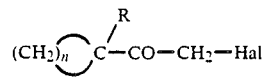
(II)

which are listed in Table 2 were obtained according to Example 1a, b and e:

TABLE 2

| Intermediate No. | n | R | Hal | Physical constants b.p. (°C.)/m-bar |
|---|---|---|---|---|
| (II-2) | 5 | CH₃ | Cl | 115° C./20 |
| (II-3) | 4 | C₄H₉ | Cl | 82–88/0.1 |
| (II-4) | 6 | CH₃ | Cl | 75–78/0.1 |
| (II-5) | 7 | CH₃ | Cl | 92–96/0.03 |

The compound of the formula

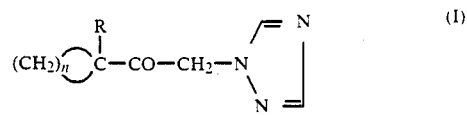
(I)

which is listed in Table 3 was obtained in an analogous manner according to Example 1:

TABLE 3

| Compound No. | n | R | Refractive Index $n_D^{20}$ |
|---|---|---|---|
| 2 | 5 | CH₃ | 1.5058 |

Conversion of other novel compounds to other fungicidally active compounds is described in detail in German Application P 31 45 890.4, filed November 19, 1981, corresponding to U.S. Application Ser. No. 438,061, filed November 1, 1982 now U.S. Pat. No. 4,465,680, the disclosure of which is incorporated herein by reference.

It will be understood that the specification and examples are illustrative but not limitative of the present invention and that other embodiments within the spirit and scope of the invention will suggest themselves to those skilled in the art.

The compound of the formula

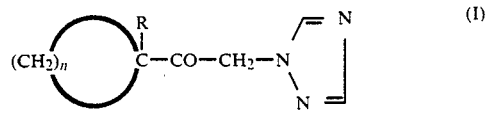
(I)

which is listed in Table 3 was obtained in an analogous manner according to Example 1:

TABLE 3

| Compound No. | n | R | Refractive Index $n_D^{20}$ |
|---|---|---|---|
| 2 | 5 | CH₃ | 1.5058 |

Conversion of other novel compounds to other fungicidally active compounds is described in detail in German Application P 31 45 890.4, filed November 19, 1981, corresponding to U.S. Application Ser. No.           , filed           , now pending, the disclosure of which is incorporated herein by reference.

It will be understood that the specification and examples are illustrative but not limitative of the present invention and that other embodiments within the spirit and scope of the invention will suggest themselves to those skilled in the art.

We claim:

1. 1-Methylcyclohexyl (1,2,4-triazol-1-yl)-methyl ketone of the formula

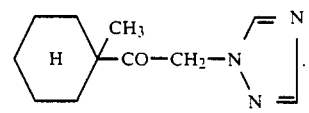

* * * * *